(12) United States Patent
Baba

(10) Patent No.: US 7,957,003 B2
(45) Date of Patent: Jun. 7, 2011

(54) NITROGEN ANALYZING APPARATUS

(75) Inventor: Naoho Baba, Tokyo (JP)

(73) Assignee: Taiyo Nippon Sanso Corporation, Tokyo (JP)

( * ) Notice: Subject to any disclaimer, the term of this patent is extended or adjusted under 35 U.S.C. 154(b) by 352 days.

(21) Appl. No.: 12/279,630

(22) PCT Filed: Feb. 9, 2007

(86) PCT No.: PCT/JP2007/052343
§ 371 (c)(1),
(2), (4) Date: Aug. 15, 2008

(87) PCT Pub. No.: WO2007/097211
PCT Pub. Date: Aug. 30, 2007

(65) Prior Publication Data
US 2010/0220320 A1  Sep. 2, 2010

(30) Foreign Application Priority Data
Feb. 20, 2006  (JP) .................................. 2006-041872

(51) Int. Cl.
*G01N 21/00* (2006.01)

(52) U.S. Cl. ...................................... 356/437

(58) Field of Classification Search .................. 356/437, 356/439, 440
See application file for complete search history.

(56) References Cited

U.S. PATENT DOCUMENTS

| 3,032,654 | A | * | 5/1962 | Fay et al. ....................... 250/373 |
| 5,412,467 | A | * | 5/1995 | Malczewski et al. ......... 356/316 |
| 6,473,175 | B1 | * | 10/2002 | Malczewski ................... 356/311 |
| 6,717,666 | B2 | * | 4/2004 | Satou et al. .................... 356/311 |
| 2003/0204370 | A1 | | 10/2003 | Yemini et al. |

FOREIGN PATENT DOCUMENTS

| JP | 7-306127 | 11/1995 |
| JP | 2002-296186 | 10/2002 |
| JP | 2004-132973 | 4/2004 |
| JP | 2005-249551 | 9/2005 |
| KR | 10-2002-0077261 | 10/2002 |

OTHER PUBLICATIONS

International Search Report for PCT/JP2007/052343, mailed Apr. 17, 2007.
Official Action, with English translation, in KR 10-2008-7021298 dated Jul. 30, 2010.

* cited by examiner

*Primary Examiner* — Roy Punnoose
(74) *Attorney, Agent, or Firm* — Nixon & Vanderhye P.C.

(57) ABSTRACT

The present invention provides a nitrogen analyzing apparatus comprising:
a nitrogen concentration measuring device configured to measure the concentration of an nitrogen impurities in a mixed gas including argon and oxygen as main components on the basis of emission intensity of a light emitted from the nitrogen impurities by an electric discharge in a discharge tube and an oxygen concentration of a sample gas introduced into the discharge tube, and a diluting oxygen-introducing device configured to add a diluting oxygen in the sample gas sampled from the mixed gas according to the oxygen concentration of the mixed gas.

6 Claims, 3 Drawing Sheets

NITROGEN ANALYZING APPARATUS

CROSS-REFERENCE TO PRIORITY APPLICATION

This is a national phase application of PCT/JP2007/052343, filed Feb. 9, 2007, which claims the benefit of Japanese Patent Application, No. 2006-041872, filed Feb. 20, 2006, each incorporated herein by reference in its entirety.

TECHNICAL FIELD

The present invention relates to a nitrogen analyzing apparatus, specifically to a nitrogen analyzing apparatus for measuring the concentration of nitrogen impurities of a mixed gas containing a trace amount of nitrogen impurities, the mixed gas containing argon and oxygen as main components. In particular, the present invention relates to a nitrogen analyzing apparatus for continuously measuring the concentration of nitrogen impurities in real time, contained in both a feed argon which is introduced into an argon column, and in a crude argon which is extracted from the argon column, wherein the argon column separates the air which is a raw material to produce argon.

Priority is claimed on Japanese Patent Application No. 2006-041872, filed Feb. 20, 2006, the content of which is incorporated herein by reference.

BACKGROUND ART

As a method for measuring a concentration of nitrogen impurities in a mixed gas containing argon and oxygen as main components, a method in which the mixed gas is introduced into an electric discharge tube, wherein the pressure is no more than the atmospheric pressure, to measure the emission intensity of light emitted by electric discharge, the light being particular to nitrogen, and the oxygen concentration of the mixed gas is measured, and then the nitrogen concentration obtained from the emission intensity of the light is corrected based on the oxygen concentration of the mixed gas, thereby accurately measuring the concentration of nitrogen impurities contained in the mixed gas, is suggested (For example, Patent Document 1).

Patent Document 1: Japanese Unexamined Patent Application, First Publication No. 2005-249551

DISCLOSURE OF THE INVENTION

Problems to be Solved by the Invention

Meanwhile, in order to control the operating state of the argon column, it is necessary for an air separation apparatus to measure the nitrogen concentration of both the feed argon which is introduced into the argon column, and the crude argon which is extracted from the argon column.

However, although the feed argon and crude argon are both mixed gases containing argon and oxygen as main components, since the concentrations of oxygen and argon in the feed argon which is composed of 80 to 95% oxygen and 0 to 5000 ppm nitrogen with the balance being argon is significantly different from that in the crude argon which is composed of no less than 90% argon and 0 to 5% nitrogen with the balance being oxygen, actually, the nitrogen impurities concentrations of the feed argon and crude argon have been measured by different means or methods.

For example, when measuring the nitrogen impurities concentration of the crude argon, the argon concentration was measured using a heat-conductivity type density meter, while the oxygen concentration was measured using a zirconia type oxygen analyzer, then the nitrogen concentration (%) was calculated by subtracting the argon concentration and oxygen concentration from 100. Therefore, the nitrogen concentrations ranging from a few ppm to several % are difficult to be analyzed precisely.

Therefore, the objective of the present invention is to provide a nitrogen analyzing apparatus able to continuously and precisely measure the nitrogen impurities concentrations of both the feed argon and crude argon using one analyzing apparatus, the nitrogen analyzing apparatus applying the analyzing method and apparatus disclosed in the Patent Document 1.

Means for Resolving the Problems

In order to achieve the above-mentioned objective, the nitrogen analyzing apparatus of the present invention comprises a nitrogen concentration measuring device configured to measure the concentration of an nitrogen impurities in a mixed gas including argon and oxygen as main components on the basis of emission intensity of a light emitted from the nitrogen impurities by an electric discharge in a discharge tube and the oxygen concentration of a sample gas introduced into the discharge tube, and a diluting oxygen-introducing device configured to add a diluting oxygen in the sample gas sampled from the mixed gas according to the oxygen concentration of the mixed gas.

In addition, the present invention preferably further comprises a three-system calibration gas-introducing passage configured to introduce pure oxygen, nitrogen balanced with oxygen and pure argon as calibration gases via a flow regulator, wherein when the mixed gas is a crude argon, the diluting oxygen is added to a sample gas sampled from the crude argon by the diluting oxygen-introducing device so that the oxygen concentration of the sample gas sampled from the crude argon is adjusted to a level the same as an oxygen concentration of a feed argon.

In addition, the present invention preferably further comprises a first introducing gas-switching device, in which a passage introducing the feed argon or crude argon into the nitrogen analyzing apparatus is connected with a first passage of the three-system calibration gas-introducing passage, and a gas introduced from the first passage of the three-system calibration gas-introducing passage is changed to any one of the calibration gas, feed argon and crude argon, and a second introducing gas-switching device, in which a passage introducing the diluting oxygen into the nitrogen analyzing apparatus is connected with a second passage of the three-system calibration gas-introducing passage, and a gas introduced from the second passage of the three-system calibration gas-introducing passage is changed to any one of the calibration gas and the diluting oxygen.

In addition, the present invention preferably further comprises a flow regulator provided on a passage introducing the feed argon and crude argon into the nitrogen analyzing apparatus, and a passage provided on the primary side of the flow regulator, the passage extracting a surplus feed argon or crude argon.

In addition, the present invention is preferable in that a passage extracting a surplus feed argon or crude argon is provided on the primary side of the flow regulator between the first introducing gas-switching device and the flow regulator.

In addition, the present invention is preferable in that the diluting oxygen is obtained from an air separation device.

In the present invention, if the oxygen concentration of the mixed gas is high, a gas sampled from the mixed gas is introduced into the discharge tube, and if the oxygen concentration of the mixed gas is low, a gas sampled from the mixed gas, and then added with the diluting oxygen is introduced into the discharge tube. In addition, in the present invention, crude argon is a gas extracted from an argon column, which is provided in an air separation apparatus, and feed argon is a gas introduced into the argon column. In addition, in the present invention, the primary side means the side of upper stream and the secondary side means the side of down stream.

Effects of the Invention

According to the nitrogen analyzing apparatus of the present invention, if the mixed gas, which the nitrogen impurities therein is to be analyzed, is the feed argon containing oxygen at a high concentration, the feed argon is introduced into the discharge tube as it is for measuring the nitrogen impurities concentration, and if the mixed gas, which the nitrogen impurities therein is to be analyzed, is the crude argon containing oxygen at a low concentration, the diluting oxygen is added to the crude argon so as to adjust the oxygen concentration of the resulting gas, which is introduced into the discharge tube, to the same level as the feed argon, thereby enabling the nitrogen analyzing apparatus to measure the nitrogen impurities concentration of the crude argon as well as the feed argon.

Therefore, it is possible for the nitrogen analyzing apparatus of the present invention to measure the nitrogen impurities concentrations of both the feed argon and crude argon using one analyzing apparatus. Further, since the oxygen concentration of the crude argon is adjusted to the same level as the feed argon to measure the nitrogen impurities concentration, the calibration gas types required can be reduced to the minimum.

BRIEF DESCRIPTION OF THE REFERENCE SYMBOLS

Figure 1:
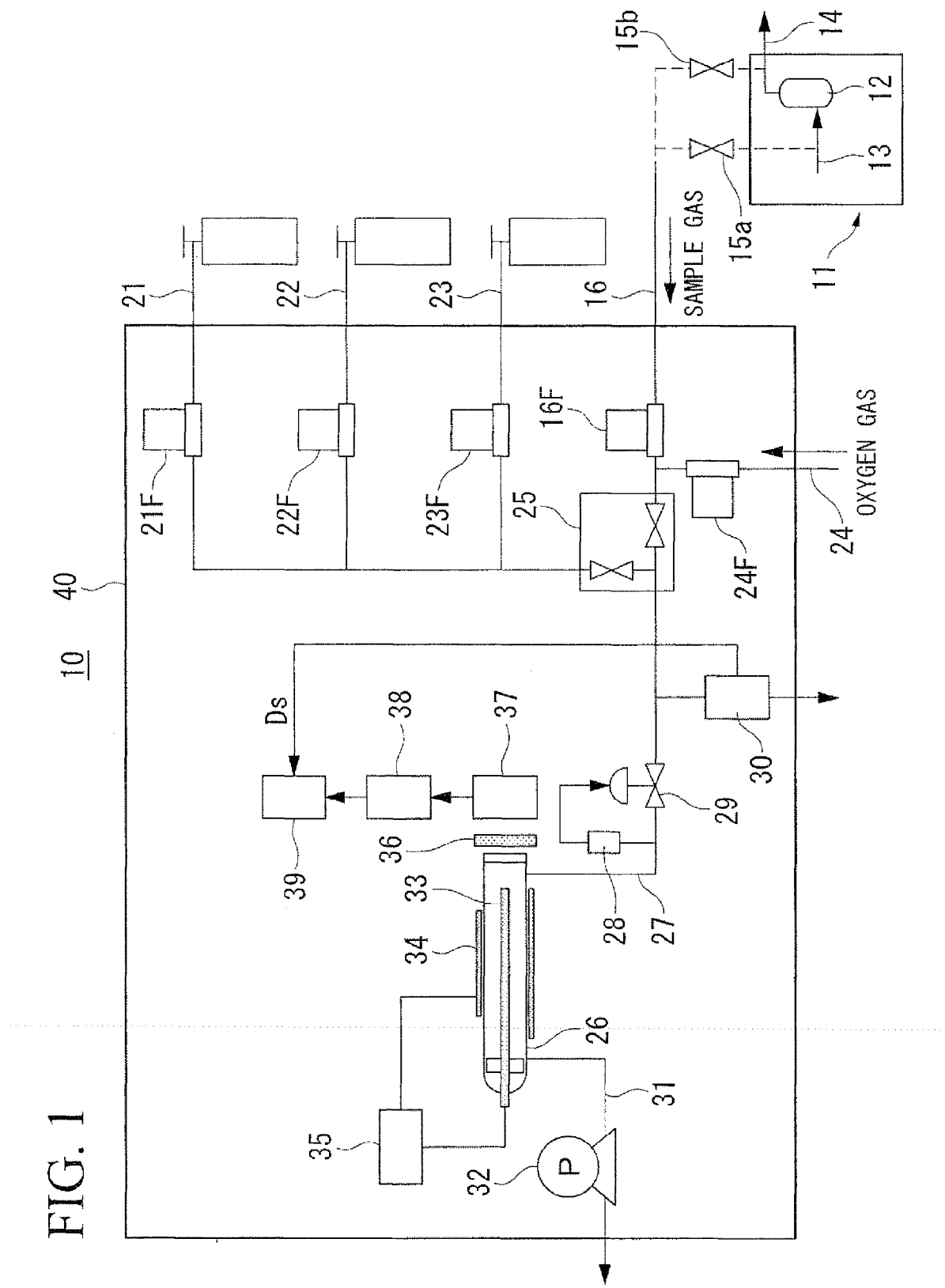
FIG. 1 is a diagram showing the first embodiment of the nitrogen analyzing apparatus of the present invention.

10: nitrogen analyzing apparatus
11: air separation apparatus
12: argon column
13, 14: passage
15a, 15b: gas switching valve
16: sample gas introducing passage
21: pure oxygen introducing passage
22: nitrogen balanced with oxygen introducing passage
23: pure argon introducing passage
24: diluting oxygen introducing passage
25: introducing gas-switching device
26: discharge tube
27: entrance side passage
28: pressure gauge
29: pressure controller
30: oxygen concentration measuring device
31: exit side passage
32: vacuum pomp
33, 34: discharge electrode
35: high-voltage alternating current power supply
36: light extracting device
37: light detector
38: signal amplifying device
39: calculator
40: constant temperature section
41: introducing gas-switching device
42: flow regulator
43: introducing gas-switching device
44: flow regulator
45: argon extracting passage
46: argon extracting valve
Ds: oxygen concentration signal
16F, 21F, 22F, 23F, 24F: flow regulator

BEST MODE FOR CARRYING OUT THE INVENTION

FIG. 1 is a diagram of the first embodiment of the nitrogen analyzing apparatus of the present invention. Nitrogen analyzing apparatus 10 is an apparatus that continuously measures the nitrogen impurities concentration of a feed argon introduced into a lower part of an argon column 12, which is provided in an air separation apparatus 11 through a passage 13, and an nitrogen impurities concentration of a crude argon, which is extracted from an upper part of the argon column 12 through a passage 14 by switching the feed argon and crude argon. The feed argon and crude argon are introduced into the nitrogen analyzing apparatus 10 through a sample gas introducing passage 16, the feed argon and crude argon passing through gas switching valves 15a and 15b.

In the nitrogen analyzing apparatus 10, three passages of a pure oxygen introducing passage 21, a nitrogen balanced with oxygen introducing passage 22 and a pure argon introducing passage 23 are provided for introducing pure oxygen, nitrogen balanced with oxygen (a predetermined amount of nitrogen is contained in oxygen) and pure argon used as calibration gases. On these calibration gas introducing passages, flow regulators 21F, 22F and 23F are provided for regulating the flows of the calibration gases to predetermined flows.

In addition, in a secondary side of a flow regulator 16F provided on a sample gas introducing passage 16, a diluting oxygen introducing passage 24 is provided for adding a diluting oxygen to a gas which is introduced through the sample gas introducing passage 16, and on the diluting oxygen introducing passage 24, a flow regulator 24F is provided for regulating the adding amount of the diluting oxygen.

In the present invention, the diluting oxygen introducing passage 24 and a flow regulator are at least provided, and an apparatus adding a diluting oxygen to a sample gas according to an oxygen concentration of a mixed gas, the sample gas being sampled from a mixed gas, is referred to as a diluting oxygen-introducing device.

The calibration gas introducing passages mentioned above and the sample gas introducing passage 16 are all connected with an entrance side passage 27 of a discharge tube 26 on the secondary side of the flow regulators via an introducing gas-switching device 25. On the entrance side passage 27, a pressure controller 29 controlling the discharge tube 26 side pressure according to the indication shown in a pressure gauge 28 and an oxygen concentration measuring device 30 measuring the oxygen concentration of the sample gas flowing through the entrance side passage 27. In addition, on the exit side passage 31 of the discharge tube 26, a vacuum pomp 32 making the inside of the discharge tube 26 to a reduced pressure condition is provided.

The discharge tube 26 is provided with discharge electrodes 33 and 34 which are attached in the inside and outside of the discharge tube 26, the discharge electrodes 33 and 34 being covered with a dielectric substance, a high-voltage alternating current power supply 35 applying a voltage to the discharge electrodes 33 and 34, a light extracting device 36 extracting light having a wavelength which is particular to nitrogen from a light generated by electric discharging, and a light detector 37 measuring a light intensity, and further provided with a signal amplifying device 38 amplifying an electric signal from the light detector 37, and a calculator 39 calculating the value of the nitrogen concentration according to the electric signal amplified by the signal amplifying device 38 and the oxygen concentration signal Ds obtained from the oxygen concentration measuring device 30.

In the present invention, the discharge tube 26, the light detector 37 and the calculator 39 are at least provided, and an apparatus for measuring the nitrogen concentration is referred to as a nitrogen concentration measuring device.

When using the nitrogen analyzing apparatus 10 to measure the concentration of the nitrogen impurities in the feed argon containing oxygen at a high concentration, the feed argon is directly introduced into the discharge tube 26 as the sample gas so as to be analyzed without adding the diluting oxygen through the diluting oxygen introducing passage 24. In addition, when measuring the nitrogen impurities concentration of the crude argon containing oxygen at a low concentration, the crude argon is added with a predetermined amount of the diluting oxygen through the diluting oxygen introducing passage 24 so as to adjust the oxygen concentration of the sample gas which is introduced to the discharge tube 26 to be analyzed, to have the same level of oxygen concentration as the feed argon.

For example, a gas composed of 9 to 10% argon and 0 to 0.5% (500 ppm) nitrogen with the balance being oxygen, which the composition thereof is significantly close to the composition of the feed argon composed of 80 to 95% oxygen and 0 to 5000 ppm nitrogen with the balance being argon, can be obtained and used as a sample gas by diluting the crude argon composed of no less than 90% argon and 0 to 5% nitrogen with the balance being oxygen 10 times using oxygen.

In this manner, when analyzing both the feed argon and crude argon, since the oxygen concentration and nitrogen concentration of the sample gases introduced into the discharge tube 26 are at the same level, the nitrogen impurities concentration of both the feed argon and crude argon can be analyzed continuously and accurately according to the emission intensity of the light from the discharge tube 26 and the oxygen concentration of the sample gas introduced into the discharge tube 26, without changing the discharge tube 26, calculator 39 and the conditions of the calibration gases.

It is acceptable for the diluting oxygen-introducing device to introduce the diluting oxygen from the outside through the diluting oxygen introducing passage 24 or introduce pure oxygen which is used as the calibration gas thorough the pure oxygen introducing passage 21. In addition, a part of the oxygen product obtained from the air separation apparatus 11 can also be used as the diluting oxygen, and when the nitrogen analyzing apparatus 10 works continuously for a long time, the oxygen product obtained from the air separation apparatus is preferably used. As the introducing gas-switching device 25, a device obtained by combining plural valves is can be used, and a three-way switching valve can also be used.

In addition, when the nitrogen analyzing apparatus 10 is used for controlling or monitoring the air separation apparatus 11, there is the case where the nitrogen analyzing apparatus 10 is set up outdoors, thus the nitrogen analyzing apparatus 10 is preferably holed in a constant temperature section 40 so as to maintain a constant temperature. In particular, because the light detector 37 which is one of the main components of the discharge tube 26 is easily affected by temperature, it is preferable to control the temperature accurately.

In addition, although a precise flow regulator, such as heat type mass flow controller, or the like, is preferably used as the flow regulators regulating the gas flow, if the pressure of the gas which is introduced to the apparatus can be maintained at a constant pressure, an orifice, for example, can be used to control the flow simply.

The discharge tube 26 is not limited to the constitution shown in FIG. 1, and a discharging device, which is able to generate an electric discharge between the electrodes covered with a dielectric substance being applied with a high voltage, can be used. For example, a discharging device, in which the cylindrical electrodes covered with a dielectric substance applied with a high voltage are facing each other, can be used, or a discharging device having a shape that two electrodes are arranged outside of the cylindrical dielectric substance in the circumferential direction and the two electrodes are insulated outside of the dielectric substance, is also can be used.

In addition, as the light extracting device 36, a device able to extract a specific wave length, such as interference filter which optionally penetrates the emission light having a wave length particular to nitrogen, a spectrometer extracting a specific wave length, or the like can be used. The wave length is preferably 337±2 nm. Further, although as the light detector 37, a photomultiplier tube is preferably used, a photo diode or photo diode array can also be used to change the light signal to an electric signal. Furthermore, a detector module, in which the light detector 37 and signal amplifying device 38 are integrated together, can also be used.

There is no restriction on the types of oxygen concentration measuring device 30 as long as the oxygen concentration measuring device 30 is able to measure the oxygen concentration. Specific examples include a sensor using a stabilized zirconia being an oxide-ion conductor, a diaphragm-seal type oxygen sensor using a strong electrolyte solution, a magnetic oxygen sensor using the triplet state of oxygen, an optical oxygen sensor using the principle which the disappearance of the fluoresce generated from the polycyclic aromatic compound or organic ruthenium complex is affected by the oxygen concentration, an oxygen sensor using a field effect transistor, and the like. These are preferably used. Further, since the feed argon and the crude argon diluted by the diluting oxygen are both mixtures including argon and oxygen at no less than 99%, the oxygen concentration can be determined by measuring the mixing ratio of the two components, therefore a sensor, such that being able to measure the mixing ratio of the two components by measuring the thermal conductivity or sound speed of the sample gas, can be used. Furthermore, the oxygen concentration can be calculated by a method, in which the emission light, which is particular to argon, is extracted from the emission lights from the discharge tube, and then the amount of argon is determined by using the light detector. The light detector can be the same as or different from the light detector used for the nitrogen measurement.

The nitrogen concentrations of the feed argon and crude argon can be obtained by correcting the nitrogen concentrations with the correction amounts which correspond to the oxygen concentrations of the feed argon and crude argon. The correction amounts can be determined from calibration curves constructed by measuring the emission intensities of the lights generated from the calibration gases having various concentrations of oxygen, argon and nitrogen. The calibration gases can be obtained by controlling the flow regulators 21F, 22F, and 23F provided on the pure oxygen introducing passage 21, nitrogen balanced with oxygen introducing passage 22 and pure argon introducing passage 23. For example, a calibration gas which does not contain nitrogen can be obtained by introducing pure oxygen or pure argon only, and calibration gases containing oxygen, argon and nitrogen at various concentrations can be obtained by regulating the flow ratios of the pure argon and the nitrogen balanced with oxygen. More specifically, for example, when the nitrogen concentration of the nitrogen balanced with oxygen is 500 ppm, three kinds of calibration gases, such as a gas including 95% oxygen, 5% argon and 475 ppm nitrogen, a gas including 90% oxygen, 10% argon and 450 ppm nitrogen, and a gas including 85% oxygen, 15% argon and 425 ppm nitrogen are obtained by controlling the flow ratios of the pure argon and the nitrogen balanced with oxygen, and introduced into the discharge tube 26 to measure the emission light intensities at various concentrations. Then the calibration curves are constructed using the emission light intensities, and the correction amounts which correspond to various oxygen concentrations are determined according to the calibration curve.

Accordingly, when analyzing the feed argon or crude argon, the nitrogen impurities concentration in the feed argon or crude argon can be measured precisely by correcting the calibration curve of nitrogen based on the oxygen concentration measured by the oxygen concentration measuring device 30. Although as the calculator 39 calculating the nitrogen concentration, a personal computer having a calculating function is preferably used, an analog circuit can also be used in the case where the relationship between the evaluated oxygen concentration and the gradient or intercept of the nitrogen calibration curve shows a linear function.

Figure 2:
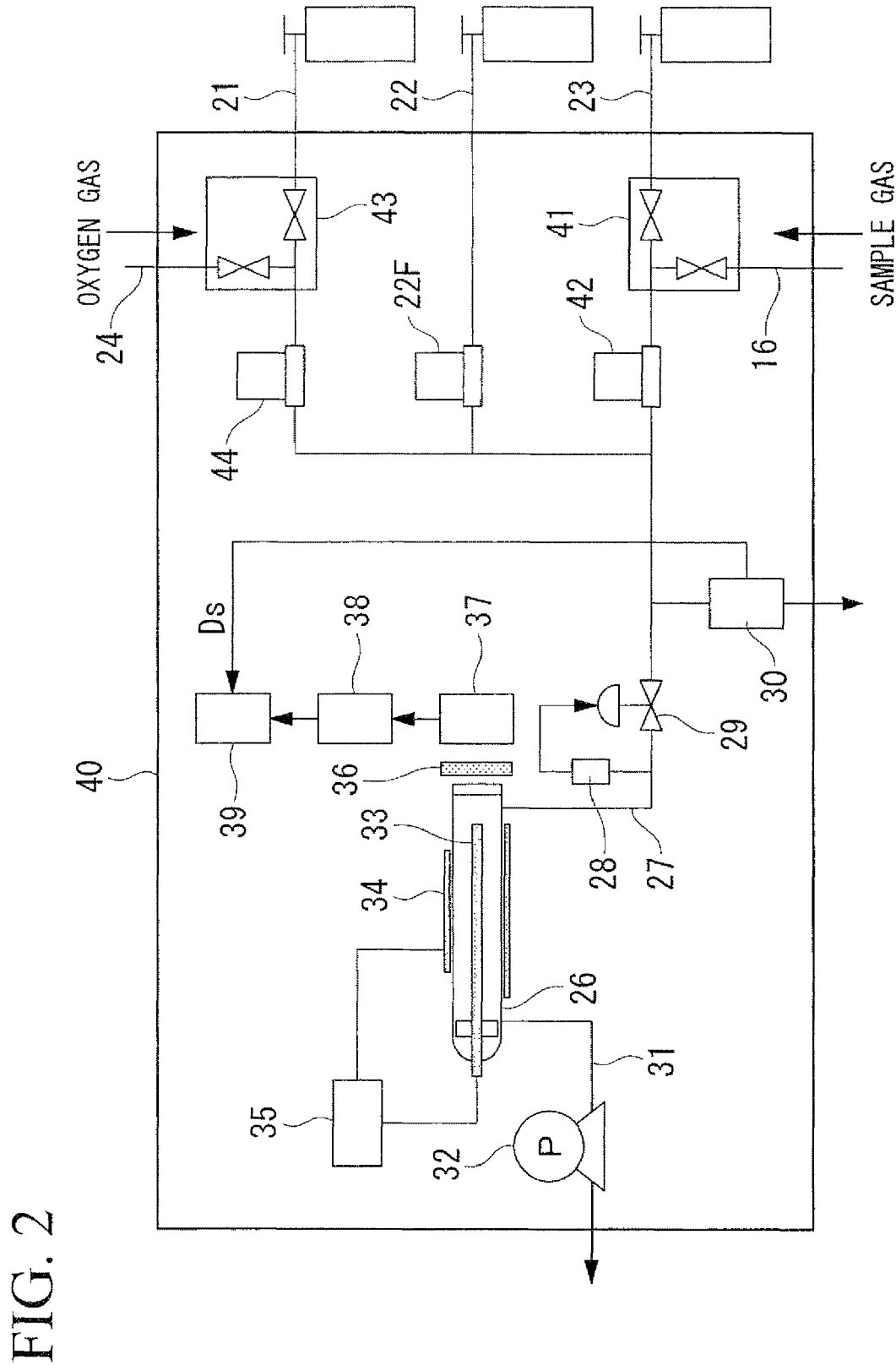
FIG. 2 is a diagram showing the second embodiment of the nitrogen analyzing apparatus of the present invention.

FIG. 2 is a diagram showing the second embodiment of the nitrogen analyzing apparatus of the present invention. In the following description, the constituent elements, which are the same as the constituent elements of the first embodiment refer to the same symbols, and the detailed descriptions are omitted.

In the nitrogen analyzing apparatus shown in this embodiment, the sample gas introducing passage 16 is connected with the pure argon introducing passage 23 through an introducing gas-switching device 41, and a flow regulator 42 regulating the flow of pure argon that is one of the calibration gases and the flow of the feed argon or crude argon is provided on the down stream side, and also the diluting oxygen introducing passage 24 is connected with the pure oxygen introducing passage 21 through an introducing gas-switching device 43, and a flow regulator 44 is provided on the down stream side for regulating the flow of pure oxygen that is one of the calibration gases and the flow of the diluting oxygen for diluting the crude argon.

Since the calibration of the nitrogen analyzing apparatus and the analysis of the sample gas are not performed at the same time, the flow regulators 42 and 44 can not only be used for the calibration, but also be used for the analysis by operating the introducing gas-switching device 41 and 43. Therefore, the required number of flow regulators which are high-priced, can be reduced, thereby realizing the cost reduction.

The sample gas introducing passage 16 and the diluting oxygen introducing passage 24 can be connected with any one of the three calibration gas introducing passages. In addition, when using pure oxygen used for calibration as the diluting oxygen, the diluting oxygen introducing passage 24 and the introducing gas-switching device 43 are unnecessary.

Figure 3:
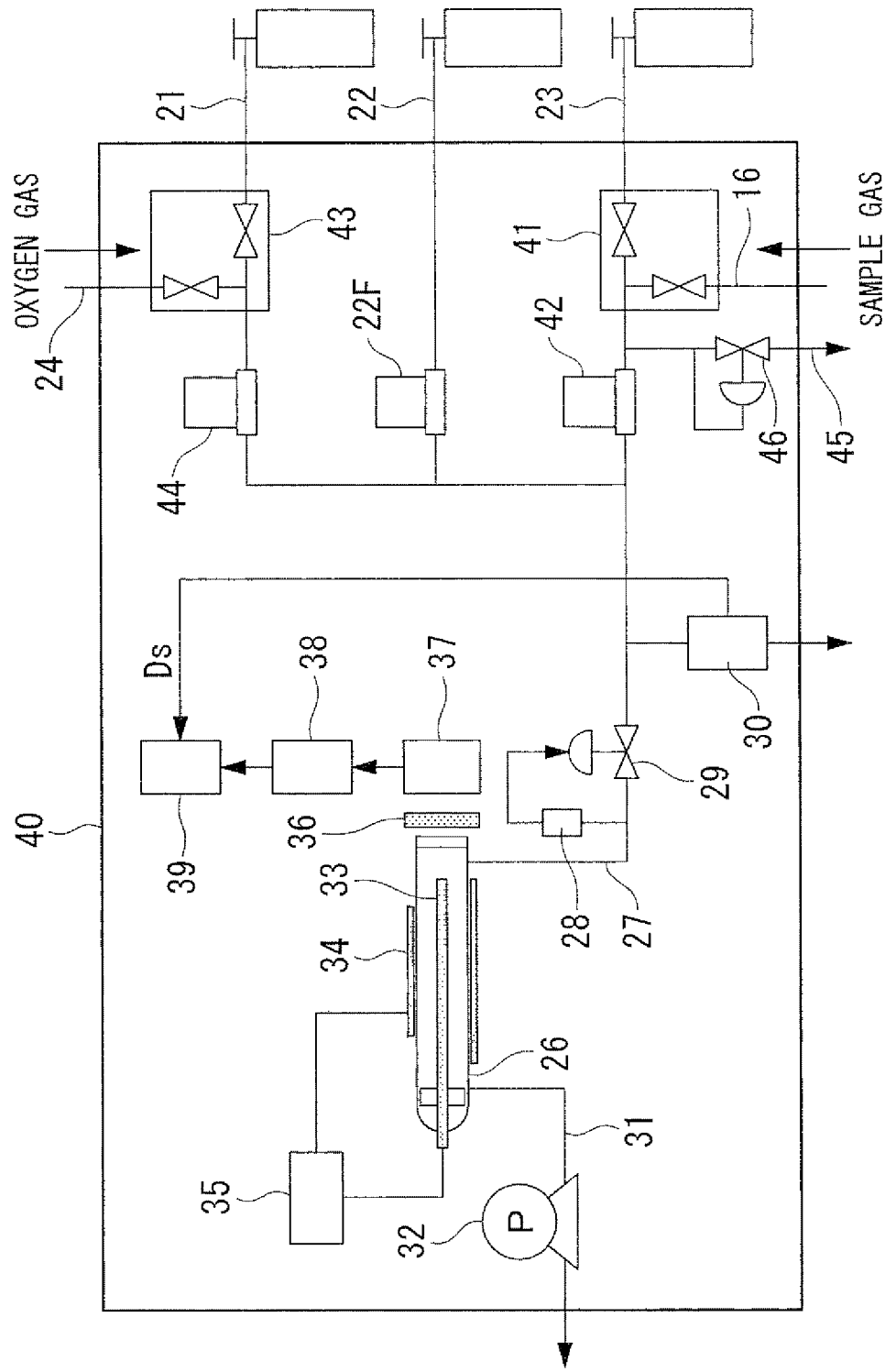
FIG. 3 is a diagram showing the third embodiment of the nitrogen analyzing apparatus of the present invention.

FIG. 3 is a diagram showing the third embodiment of the nitrogen analyzing apparatus of the present invention. The nitrogen analyzing apparatus of this embodiment is configured in such a manner that the second embodiment of the nitrogen analyzing apparatus is further provided with an argon extracting passage 45 on the primary side of the flow regulator 42, the argon extracting passage 45 extracting the surplus of feed argon and crude argon to the outside of the nitrogen analyzing apparatus by opening an argon extracting valve 46.

By providing the argon extracting passages 45, even in the case where the duration of the time between sampling and analyzing is long due to the long distance between the feed argon or crude argon sampling place and the nitrogen analyzing apparatus, it is possible to extract the excessive feed argon and crude argon through the argon extracting passage 45. Accordingly, it is possible to shorten the arrival time by raising the flow rate of the feed argon and crude argon, which is introduced through the sample gas introducing passage 16, and also, it is possible to improve the control responsibility of the air separation apparatus 11. In addition, the argon extracting passage 45 can also be provided on the primary side of the flow regulator 16F, which is provided on the sample gas introducing passage 16 shown in FIG. 1. In addition, a back pressure valve can be used as the argon extracting valve 46.

INDUSTRIAL APPLICABILITY

According to the nitrogen analyzing apparatus of the present invention, it is possible to measure the nitrogen impurities concentrations of both feed argon and crude argon using one analyzing apparatus. Further, since the oxygen concentration of the crude argon is adjusted to the same level of the feed argon when measuring the impurity concentration, the calibration gas types required can be reduced to the minimum, which is of great industrial significance.

The invention claimed is:

1. A nitrogen analyzing apparatus comprising:
   a nitrogen concentration measuring device configured to measure the concentration of an nitrogen impurities in a mixed gas including argon and oxygen on the basis of emission intensity of a light emitted from the nitrogen impurities by an electric discharge in a discharge tube and an oxygen concentration of a sample gas introduced into the discharge tube, and
   a diluting oxygen-introducing device configured to add a diluting oxygen in the sample gas sampled from the mixed gas according to the oxygen concentration of the mixed gas.

2. The nitrogen analyzing apparatus according to claim 1, further comprising:
   a three-way calibration gas-introducing passage configured to introduce a pure oxygen, a nitrogen balanced with oxygen and a pure argon as calibration gases respectively via a flow regulator, wherein
   when the mixed gas is a crude argon, the diluting oxygen is added to a sample gas sampled from the crude argon by the diluting oxygen-introducing device so that the oxygen concentration of the sample gas sampled from the crude argon is adjusted to a level the same as the oxygen concentration of a feed argon.

3. The nitrogen analyzing apparatus according to claim 2, further comprising:
   a first introducing gas-switching device, in which a passage introducing the feed argon or crude argon into the nitrogen analyzing apparatus is connected with a first passage of the three-way calibration gas-introducing passage, and a gas introduced from the first passage of the three-way calibration gas-introducing passage is changed to any one of the calibration gas, feed argon and crude argon, and a second introducing gas-switching device, in which a passage introducing the diluting oxygen into the nitrogen analyzing apparatus is connected with a second passage of the three-way calibration gas-introducing passage, and a gas introduced from the second passage of the three-way calibration gas-introducing passage is changed to any one of the calibration gas and the diluting oxygen.

4. The nitrogen analyzing apparatus according to claim 2, further comprising:

a flow regulator provided on a passage introducing the feed argon and crude argon into the nitrogen analyzing apparatus, and a passage provided on the primary side of the flow regulator, the passage extracting a surplus feed argon or crude argon.

5. The nitrogen analyzing apparatus according to claim 3, wherein a passage extracting a surplus feed argon or crude argon is provided on the primary side of the flow regulator.

6. The nitrogen analyzing apparatus according to claim 2, wherein the diluting oxygen is obtained from an air separation device.

* * * * *